US008247617B2

(12) United States Patent
Lei et al.

(10) Patent No.: US 8,247,617 B2
(45) Date of Patent: Aug. 21, 2012

(54) GROUP 2 METAL PRECURSORS FOR DEPOSITING MULTI-COMPONENT METAL OXIDE FILMS

(75) Inventors: Xinjian Lei, Vista, CA (US); Liam J. Quinn, Taipei (TW); Daniel P. Spence, Carlsbad, CA (US)

(73) Assignee: Air Products and Chemicals, Inc., Allentown, PA (US)

(*) Notice: Subject to any disclaimer, the term of this patent is extended or adjusted under 35 U.S.C. 154(b) by 958 days.

(21) Appl. No.: 12/266,058

(22) Filed: Nov. 6, 2008

(65) Prior Publication Data

US 2009/0130338 A1 May 21, 2009

Related U.S. Application Data

(63) Continuation-in-part of application No. 12/113,397, filed on May 1, 2008.

(60) Provisional application No. 60/938,233, filed on May 16, 2007.

(51) Int. Cl.
*C07C 49/00* (2006.01)
*C07F 5/00* (2006.01)
*C07F 5/06* (2006.01)

(52) U.S. Cl. .................... 568/412; 534/15; 549/206
(58) Field of Classification Search .................. None
See application file for complete search history.

(56) References Cited

U.S. PATENT DOCUMENTS

| 5,139,999 | A | 8/1992 | Gordon et al. |
| 5,248,787 | A | 9/1993 | Timmer et al. |
| 5,252,733 | A | 10/1993 | Norman et al. |
| 5,453,494 | A | 9/1995 | Kirlin et al. |
| 6,214,105 | B1 | 4/2001 | Hintermaier et al. |
| 6,218,518 | B1 | 4/2001 | Baum et al. |
| 6,277,436 | B1 | 8/2001 | Stauf et al. |
| 6,338,873 | B1 | 1/2002 | Paw et al. |
| 6,344,079 | B1 | 2/2002 | Baum |
| 2006/0292303 | A1 | 12/2006 | Millward et al. |

FOREIGN PATENT DOCUMENTS

| EP | 0 405 634 A2 | 1/1991 |
| JP | 2000100802 | 4/2000 |
| WO | 93/04072 A | 3/1993 |

OTHER PUBLICATIONS

A.A. Drozdov et al, New oligomeric structures of barium dipivaloylmethanate, Ba4(thd)8, and its pivalate derivative Ba5(thd)9(piv), Polyhedron, 1992, vol. 11 No. 22, pp. 2877-2882.

G. Rossetto et al, Studies on molecular barium precursors for MOCVD: synthesis and characterization of barium . . . , Polyhedron, 1992, vol. 11 No. 8, pp. 979-985.

John Auld et al, Vapour-phase transport of barium b-diketonates in the deposition of oxides and the isolation and structure characterization of a novel . . . , J. Mater. Chem., 1993, 3(12), pp. 1203-1208.

(Continued)

*Primary Examiner* — Paul A Zucker
*Assistant Examiner* — Jennifer C Sawyer
(74) *Attorney, Agent, or Firm* — Joseph D. Rossi

(57) ABSTRACT

Novel Sr and Ba complexes containing both beta-diketonates and N-methyl-pyrrolidone were synthesized and characterized. TGA experiments indicated these complexes are volatile, they can be employed as precursors for ALD strontium titanate (STO) or barium strontium titanate films (BST) films in semiconductor fabrication.

16 Claims, 5 Drawing Sheets

OTHER PUBLICATIONS

Simon R. Drake et al, Monomeric group IIA metal b-diketonates stabilized by multidendate glymes, Inorg. Chem., 1993, 32, pp. 3227-3235.

Robin A. Gardiner et al, Mononuclear barium diketonate polyamine adducts. Synthesis, structures, and use in MOCVD of barium titanate, Chem. Mater. 1994, 6, pp. 1967-1970.

L.G. Hubert-Pfalzgraf et al, Barium b-diketonate derivatives with aminoalcohols: synthesis, molecular structure and thermal behaviour of . . . , Polyhedron 1994, vol. 13, No. 14, pp. 2163-2172.

Jonathon Brooks et al, The crystal structure of unadducted strontium bis-tetramethylheptanedionate: the standard precursor for the MOCVD of strontium-containing oxides, Chem. Vap. Deposition, 2000, 6, No. 2, pp. 66-69.

Y.-S. Min et al, Liquid source-MOCVD of BaxSr1-xTiO3 (BST) thin films with a N-alkoxy-B-ketoiminato titanium complex, Chem. Vap. Deposition 2001, 7, No. 4, pp. 146-149.

Cheol Seong Hwang et al, Cation composition control of MOCVD (Ba,Sr) TiO3 thin films along the capacitor hole, J. Electrochemical Soc. 2002, 149 (10) pp. G585-G592.

Cedric Bedoya et al, MOCVD of Sr-containing oxides: tranport properties and deposition mechanisms of the Sr (tmhd)2 pmdeta precursor, Chem. Vap. Deposition 2005, 11, pp. 269-275.

Oh Seong Kwon et al, Chemically conformal ALD of SrTiO3 thin films using conventional metallorganic precursors, J. Electrochemical Soc. 2005, 152 (4) C229-C236.

Oh Seong Kwon et al, Atomic layer deposition and electrical properties of SrTiO3 thin films grown using Sr (C11H19O2)2, . . . , J. Electrochemical Soc. 2007, 154 (6) G127-G133.

S.B. Turnipseed et al, Synthesis and characterization of alkaline-earth-metal B-diketonate complexes used as precursors for chemical vapor deposition of thin-film superconductors, Inorg. Chem. 1991, 30, pp. 1164-1170.

Cheol Seong Hwang et al, Compositional variation of metallorganic chemically vapor deposited SrTiO3 thin films along the capacitor hole having a diameter of 0.15 pm, J. Electrochemical Soc. 2001, 148, (11) pp. G636-G639.

Timothy E. Glassman et al, Evidence for cooperative oxidation of MOCVD precursors used in BaxSr1-xTiO3 film growth, Mat. Res. Soc. Symp. Proc. vol. 446, 1997, pp. 321-326.

G Bhandari et al, Comparison of (L)M(thd)2 (M=Mg, Ca, Sr, Ba; L=TETRAGLYME, PMDETA) precursors for high K dielectric MOCVD, Mat. Res. Soc. Symp. Proc. vol. 446, 1997, pp. 327-322.

Sadique R.A., et al; "Monomeric and Dimeric Amidinate Complexes of Magnesium"; Inorg. Chem.; vol. 40; pp. 6349-6355; Nov. 26, 2001; XP002495310.

GROUP 2 METAL PRECURSORS FOR DEPOSITING MULTI-COMPONENT METAL OXIDE FILMS

CROSS REFERENCE TO RELATED APPLICATIONS

This patent application is a continuation-in-part of U.S. patent application Ser. No. 12/113,397, filed on May 1, 2008 which, in turn, claims the benefit of priority under 35U.S.C. §119(e) of U.S. Provisional Patent Application Ser. No. 60/938,233, filed on May 16, 2007.

BACKGROUND OF THE INVENTION

The semiconductor fabrication industry has an interest in depositing barium strontium titanate films ("BST") for constructing various electronic devices in integrated circuits. The industry has sought precursors of barium strontium and titanium that are stable, liquid and readily decompose under standard deposition conditions leaving high purity BST films and removing in the vapor phase the remainder of the precursors of barium, strontium and titanium, typically in the form of ligands that reversibly bind the metals until the deposition conditions are provide wherein the metal is deposited from the ligand precursor resulting in essentially deposited metal and volatile, gas phase leaving groups constituting the ligand that bound the metal in the precursor form or decomposition components of the ligand which still exhibit the properties of being good leaving groups that do not contaminate the deposited BST film and typically leave as volatile, gaseous groups.

Representative art to this field includes:

Auld, J.; Jones, A. C.; Leese, A. B.; Cockayne, B.; Wright, P. J.; O'Brien, P.; Motevalli, M., "Vapor-phase transport of barium b-diketonates in the deposition of oxides and the isolation and structural characterization of a novel hexameric cluster of 2,2,6,6-tetramethylheptane-3,5-dionato-barium(II)", *Journal of Materials Chemistry*, 3, (12), 1203-8, (1993).

Baum, T. H., "Alkane and polyamine solvent compositions for liquid delivery chemical vapor deposition", U.S. Pat. No. 6,344,079 (2002).

Baum, T. H.; Paw, W., "Group IIA β-diketonate tetrahydrofuran-adduct complexes as source reagents for chemical vapor deposition", U.S. Pat. No. 6,218,518 (2001).

Bedoya, C.; Condorelli, G. G.; Motta, A.; Mauro, A. D.; Anastasi, G.; Fragalà, I. L.; Lisoni, J. G.; Wouters, D., "MOCVD of Sr-Containing Oxides: Transport Properties and Deposition Mechanisms of the Sr(tmhd)$_2$·pmdeta Precursor", *Chemical Vapor Deposition*, 11, 269-275, (2005).

Brooks, J.; Davies, H. O.; Leedham, T. J.; Jones, A. C.; Steiner, A., "The crystal structure of unadducted strontium bis-tetramethylheptanedionate: The standard precursor for the MOCVD of strontium-containing oxides", *Chemical Vapor Deposition*, 6, (2), 66+, (2000).

Cheol Seong, H.; Jaehoo, P.; Doo Sup, H.; Cha Young, Y., Compositional Variation of Metallorganic Chemically Vapor Deposited SrTiO$_3$ Thin Films along the Capacitor Hole Having a Diameter of 0.15 mu m. In ECS: (2001); Vol. 148, pp G636-G639.

Drake, S. R.; Miller, S. A. S.; Williams, D. J., "Monomeric Group IIA metal β-diketonates stabilized by multidentate glymes", *Inorganic Chemistry*, 32, (15), 3227-35, (1993).

Drozdov, A. A.; Trojanov, S. I., "New oligomeric structures of barium dipivaloylmethanate, Ba$_4$(tmhd)$_8$, and its pivalate derivative Ba$_5$(tmhd)$_9$(piv)", Polyhedron 11, 2877-2882 (1992).

Gardiner, R. A.; Gordon, D. C.; Stauf, G. T.; Vaartstra, B. A., "Mononuclear Barium Diketonate Polyamine Adducts—Synthesis, Structures, and Use in MOCVD of Barium-Titanate", *Chemistry of Materials*, 6, (11), 1967-1970, (1994).

Ghandari, G.; Glassman, T. E.; Studebaker, D. B.; Stauf, G.; Baum, T. H., "Comparison of (L)M(tmhd)$_2$(M=Mg, Ca, Sr, Ba; L=tetraglyme, pmdeta) precursors for high K dielectric MOCVD", *Materials Research Society Symposium Proceedings*, 446, (Amorphous and Crystalline Insulating Thin Films—1996), 327-332, (1997).

Glassman, T. E.; Bhandari, G.; Baum, T. H., "Evidence for cooperative oxidation of MOCVD precursors used in Ba$_x$Sr$_{1-x}$TiO$_3$ film growth", *Materials Research Society Symposium Proceedings*, 446, (Amorphous and Crystalline Insulating Thin Films—1996), 321-326, (1997).

Hintermaier, F. S.; Baum, T. H., "Alkane and polyamine solvent compositions for liquid delivery chemical vapor deposition", U.S. Pat. No. 6,214,105 (2001).

Hubertpfalzgraf, L. G.; Labrize, F., "Barium Beta-Diketonate Derivatives with Aminoalcohols—Synthesis, Molecular-Structure and Thermal-Behavior of Ba$_5$($\mu_4$—OH)($\mu_3$,$\eta^2$—OCH(Me)CH$_2$NMe$_2$)$_4$($\mu$, $\eta^2$-tmhd)$_4$($\eta^2$-tmhd) and of [Ba($\mu$, $\eta^2$:$\eta^2$-tmhd)($\eta^2$-tmhd)($\eta^2$—OHCH(Me)CH$_2$NMe$_2$)]$_2$", *Polyhedron*, 13, (14), 2163-2172, (1994).

Hwang, C. S.; No, S. Y.; Park, J.; Kim, H. J.; Cho, H. J.; Han, Y. K.; Oh, K. Y., "Cation Composition Control of MOCVD (Ba,Sr)TiO$_3$ Thin Films along the Capacitor Hole", *Journal of The Electrochemical Society*, 149, (10), G585-G592, (2002).

Kwon, O, S.; Kim, S. K.; Cho, M.; Hwang, C. S.; Jeong, J., "Chemically Conformal ALD of SrTiO$_3$ Thin Films Using Conventional Metallorganic Precursors", *Journal of The Electrochemical Society*, 152, (4), C229-C236, (2005).

Kwon, O, S.; Lee, S. W.; Han, J. H.; Hwang, C. S., "Atomic Layer Deposition and Electrical Properties of SrTiO$_3$ Thin Films Grown Using Sr(C$_{11}$H$_{19}$O$_2$)$_2$, Ti(Oi-C$_3$H$_7$)$_4$, and H$_2$O", *J. Electrochem. Soc.*, 154, G127-G133, (2007).

Min, Y.-S.; Cho, Y. J.; Kim, D.; Lee, J.-H.; Kim, B. M.; Lim, S. K.; Lee, I. M.; Lee, W. I., "Liquid source-MOCVD of Ba$_x$Sr$_{1-x}$TiO$_3$ (BST) thin films with a N-alkoxy-b-ketoiminato titanium complex", *Chemical Vapor Deposition*, 7, (4), 146-149, (2001).

Ohkawa, A.; Tsutsumi, Y., "Deposition of thin films in fabrication of semiconductor devices by MOCVD process", 98-263702 2000100802, 19980917, (2000).

Paw, W.; Baum, T. H., "Preparation of Group IIA metal b-diketonate Lewis base MOCVD source reagents, and method of forming Group IIA metal-containing films utilizing same", U.S. Pat. No. 6,338,873 (2002).

Rossetto, G.; Polo, A.; Benetollo, F.; Porchia, M.; Zanella, P., "Studies on Molecular Barium Precursors for Mocvd—Synthesis and Characterization of Barium 2,2,6,6-Tetramethyl-3,5-Heptanedionate—X-Ray Crystal-Structure of [Ba(tmhd)$_2$.Et$_2$O]$_2$", *Polyhedron*, 11, (8), 979-985, (1992).

Stauf, G. T.; Roeder, J. F.; Baum, T. H., "Liquid delivery MOCVD process for deposition of high frequency dielectric materials", U.S. Pat. No. 6,277,436 (2001).

BRIEF SUMMARY OF THE INVENTION

The present invention is directed to a metal containing complex represented by a structure selected from the group consisting of:

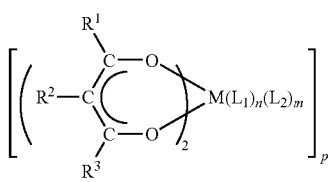

A wherein M is selected from Mg, Ca, Sr, and Ba; $R^1$ and $R^3$ are independently selected from the group consisting of $C_1$-$C_{10}$ linear or branched alkyl, $C_1$-$C_{10}$ alkoxyalkyl, $C_1$-$C_{10}$ fluoroalkyl, $C_4$-$C_{12}$ cycloaliphatic, and $C_4$-$C_{12}$ aryl; $R^2$ is selected from the group consisting of hydrogen, $C_1$-$C_{10}$ linear or branched alkyl, $C_1$-$C_{10}$ fluoroalkyl, $C_1$-$C_{10}$ alkoxy, $C_4$-$C_{12}$ cycloaliphatic, and $C_6$-$C_{12}$ aryl; $L_1$ is selected from the group consisting of an organic amide having a formula RCONR'R" wherein R and R' are independently linear or branched alkyl having from 1-10 carbon atoms wherein R and R' can be connected to form a cyclic group having from 4 to 6 atoms, and R" is selected from $C_1$-$C_4$ alkyl and $C_3$-$C_8$ cycloalkyl; $L_2$ is selected from the group consisting of $H_2O$ and ROH wherein R is a $C_1$-$C_{10}$ linear or branched alkyl group or a cyclic group having from 4 to 6 atoms, and an organic amide having a formula RCONR'R" wherein R and R' are linear or branched alkyl having from 1-10 carbon atoms wherein R and R' can be connected to form a cyclic group having from 4 to 6 atoms, and R" is selected from the group consisting of a $C_1$-$C_4$ alkyl and a $C_4$-$C_8$ cycloalkyl; n is a number selected from between 1 and 4; m is selected from a number between 0 to 4, and p is selected from 1 and 2;

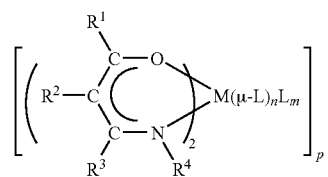

B wherein M is selected from Mg, Ca, Sr, and Ba; $R^1$, $R^3$, and $R^4$ are independently selected from the group consisting of $C_1$-$C_{10}$ linear or branched alkyl, $C_1$-$C_{10}$ alkoxyalkyl, $C_1$-$C_{10}$ fluoroalkyl, $C_4$-$C_{12}$ cycloaliphatic, and $C_4$-$C_{12}$ aryl; $R^2$ is selected from the group consisting of hydrogen, $C_1$-$C_{10}$ linear or branched alkyl, $C_1$-$C_{10}$ fluoroalkyl, $C_1$-$C_{10}$ alkoxy, $C_4$-$C_{12}$ cycloaliphatic, and $C_4$-$C_{12}$ aryl; L is selected from the group consisting of an organic amide having the formula RCONR'R" wherein R and R' are independently linear or branched alkyl having from 1-10 carbon atoms wherein R and R' can be connected to form a cyclic group having from 4 to 6 atoms, and R" is selected from the group consisting of $C_1$-$C_4$ alkyl and $C_4$-$C_8$ cycloalkyl; n is a number selected from between 0 and 4; m is selected from a number between 1 to 4, or n is a number selected from between 1 and 4 and m is a number selected from between 0 to 4; p is selected from 1, 2; and µ-L indicates that L is connected to two metals, M, via µL's oxygen atom when p=2; and,

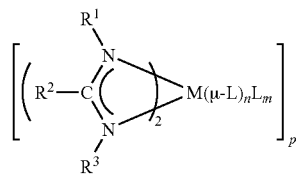

C wherein M is selected from Mg, Ca, Sr, and Ba; $R^1$ and $R^3$ are independently selected from the group consisting of $C_1$-$C_{10}$ linear or branched alkyl, $C_1$-$C_{10}$ alkoxyalkyl, $C_1$-$C_{10}$ fluoroalkyl, $C_4$-$C_{12}$ cycloaliphatic, and $C_4$-$C_{12}$ aryl; $R^2$ is selected from the group consisting of hydrogen, $C_1$-$C_{10}$ linear or branched alkyl, $C_1$-$C_{10}$ fluoroalkyl, $C_1$-$C_{10}$ alkoxy, $C_4$-$C_{12}$ cycloaliphatic, and $C_4$-$C_{12}$ aryl; L is selected from the group consisting of an organic amide having the formula RCONR'R" wherein R and R' are independently linear or branched alkyl having from 1-10 carbon atoms wherein R and R' can be connected to form a cyclic group having from 4 to 6 atoms, and R" is selected from the group consisting of $C_1$-$C_4$ alkyl and $C_4$-$C_8$ cycloalkyl; n is a number selected from between 0 and 4; m is selected from a number between 1 to 4, or n is a number selected from between 1 and 4 and m is a number selected from between 0 to 4; p is selected from 1 and 2; and µ-L indicates L is connected to two metals, M, via µL's oxygen atom when p=2.

In a preferred embodiment, for each of Structures A, B, and C, n+m=4 or less. Preferably, where p=2, n is a number selected from between 1 and 2, and m is a number selected from between 0 and 2.

In another aspect, the present invention provides a vapor deposition process for forming a conformal multi-component metal oxide thin film on a substrate wherein at least two metal containing complexes and an oxygen containing agent are introduced to a deposition chamber and a multi-component metal oxide film is deposited on a substrate, the improvement which comprises using at least two metal containing complexes, having different metals, selected from Structure A, B, and C, above.

DETAILED DESCRIPTION OF THE INVENTION

Figure 1:
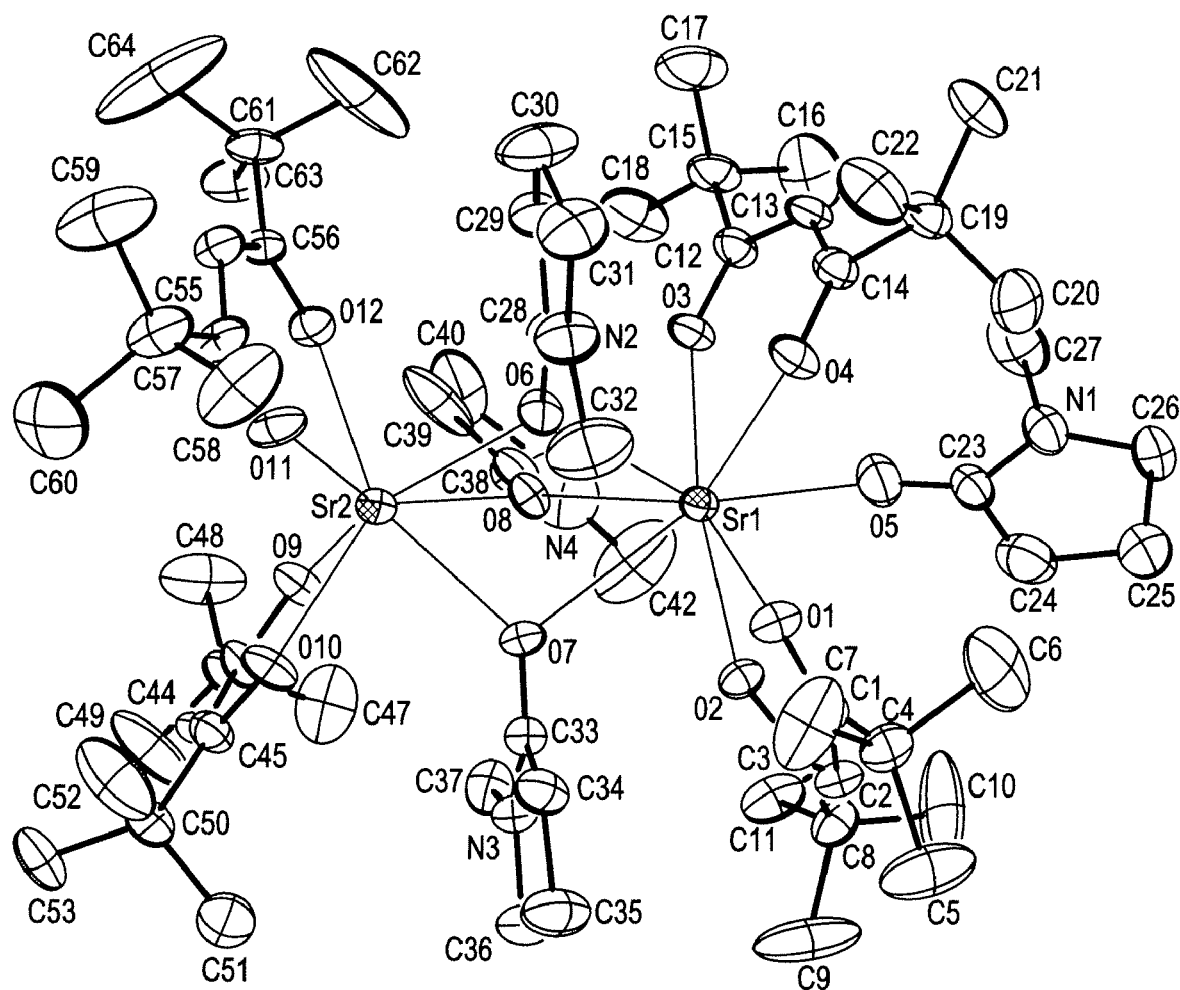
FIG. 1 is a drawing representative of the crystal structure of $Sr_2(tmhd)_4(NMP)_4$.
Figure 2:
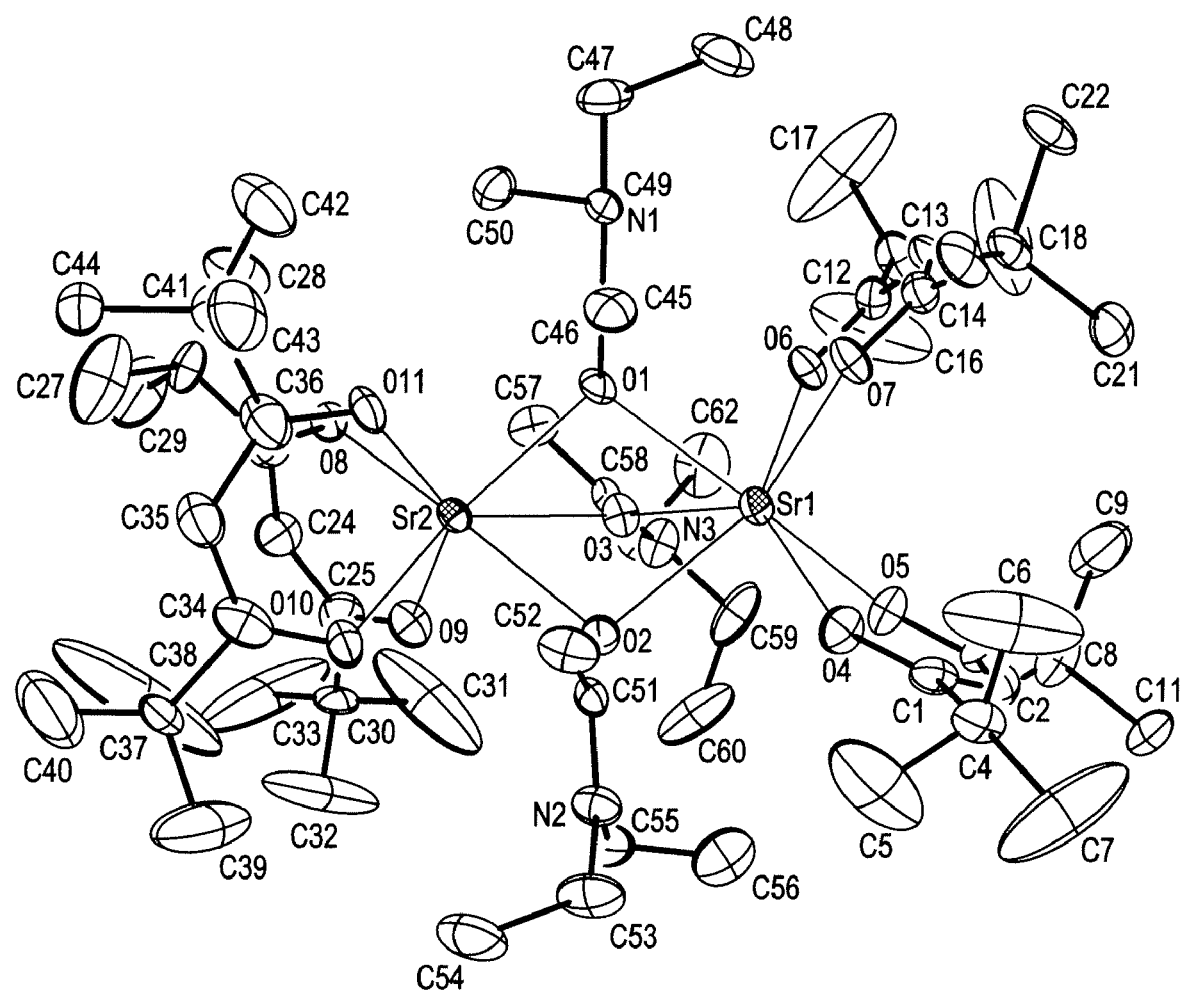
FIG. 2 is a drawing representative of the crystal structure of $Sr_2(tmhd)_4(DEAC)_3$.
Figure 3:
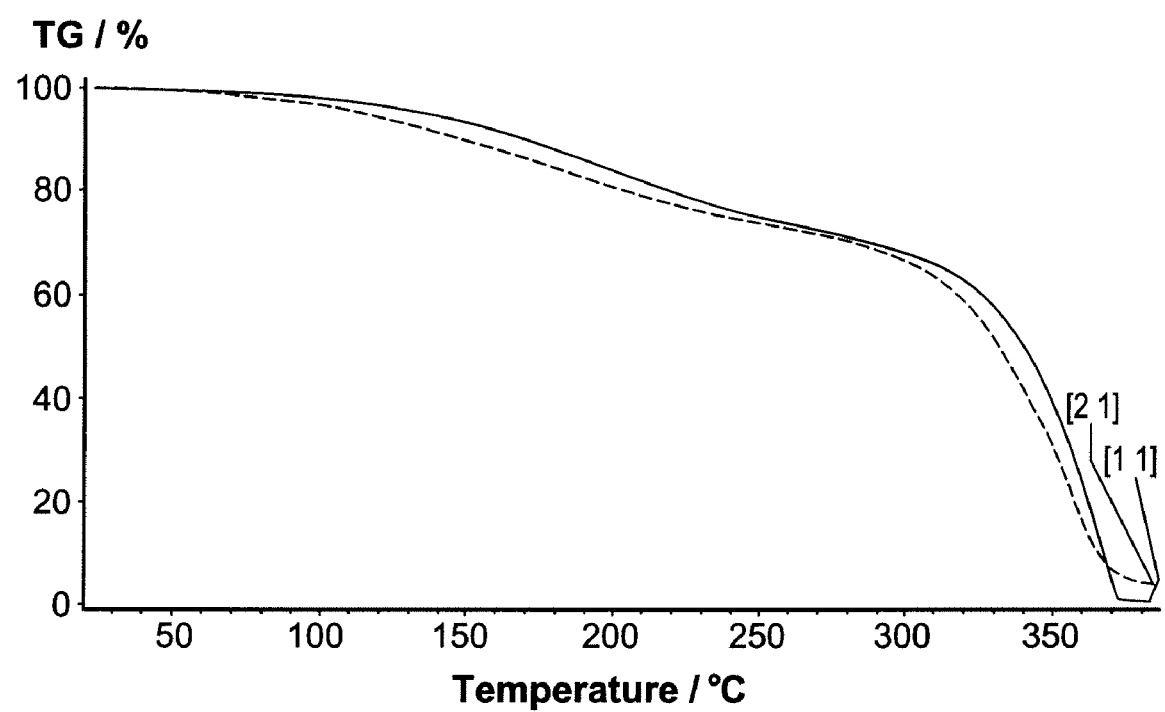
FIG. 3 is TGAs of $Sr_2(tmhd)_4(NMP)_4$ (dashed line) and $Sr_2(tmhd)_4(DEAC)_3$ (solid line), showing both are volatile complexes.
Figure 4:
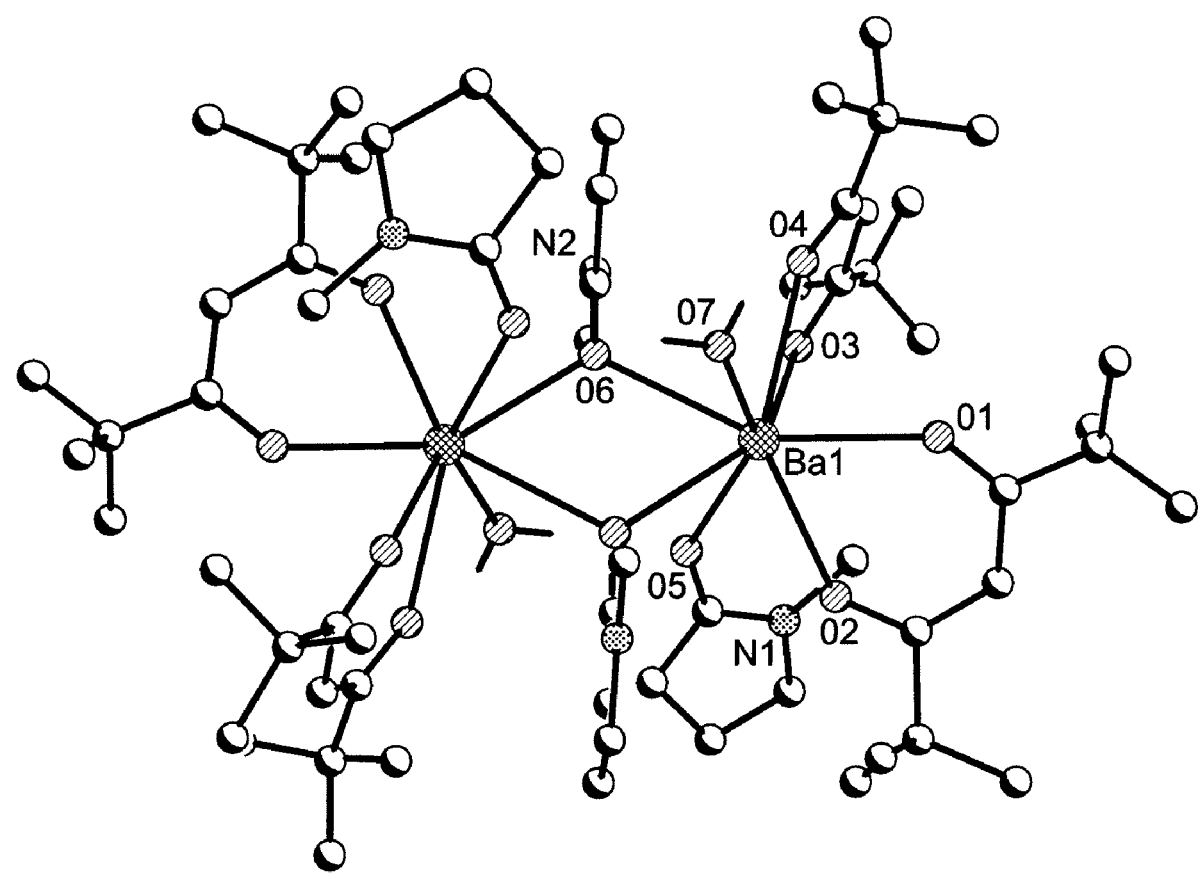
FIG. 4 is a drawing representative of the crystal structure of $[Ba(tmhd)_2(NMP)_2.H_2O]_2$.
Figure 5:
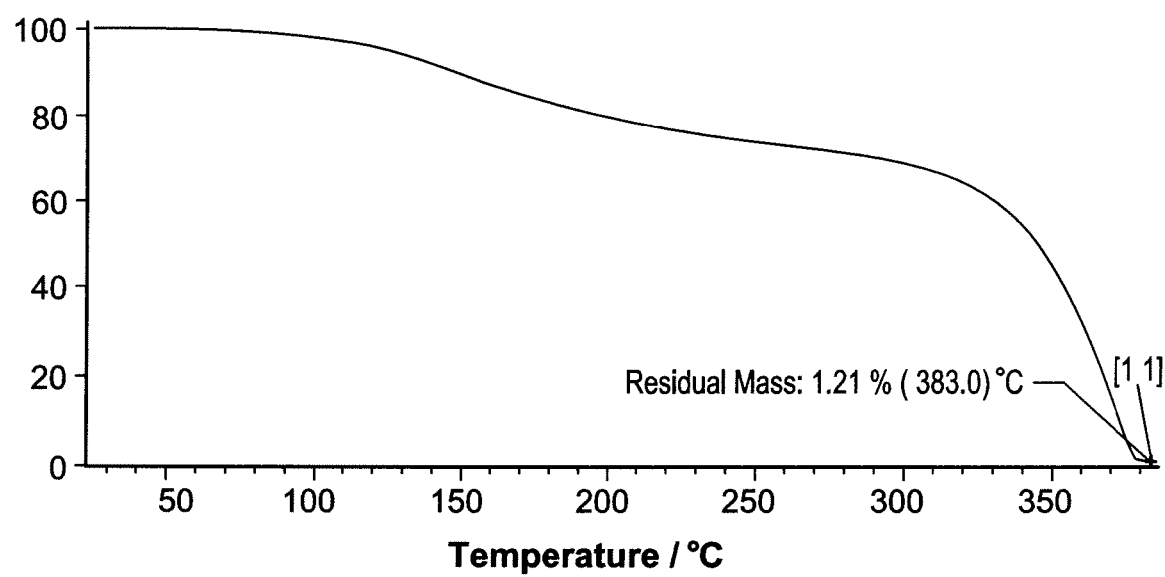
FIG. 5 is TGA of $[Ba(tmhd)_2(NMP)_2.H_2O]_2$, indicating that it is volatile.

Novel Sr and Ba complexes containing both beta-diketonates and N-methyl-pyrrolidone have been synthesized and characterized. Thermogravimetric Analysis (TGA) experiments indicate these complexes are volatile, and that they can be employed as precursors for chemical vapor deposition (CVD), cyclic chemical vapor deposition (CCVD), or atomic layer deposition (ALD) of strontium titanate (STO) or barium strontium titanate films (BST) films in semiconductor fabrication. In the deposition of STO and BST films, the titanium source is selected from titanium containing precursors exemplified by titanium alkoxides or beta-diketonates such as Ti(OPr$^i$)$_4$, Ti(tmhd)$_2$(OPr$^i$)$_2$, where Pr$^i$=isopropyl, where tmhd=2,2,6,6-tetramethyl-3,5-heptanedionate, Ti(mpd)(tmhd)$_2$, where mpd=2-methyl-2,4-pentanedioxy, Ti(4-(2-methylethoxy)imino-2-pentanoate)$_2$, and analogous titanium ligands and derivatives.

These Group 2 metal complexes are precursors capable of depositing Group 2 metal-containing films for semiconductor applications. The metal complexes include:

(i) Group 2 beta-diketonate with organic amides as adducts with a formula of [M(R$^1$C(O)CR$^2$C(O)R$^3$)$_2$(L$_1$)$_n$(L$_2$)$_m$]$_p$ wherein M is selected from Mg, Ca, Sr, and Ba; R$^1$ and R$^3$ are independently selected from the group consisting of C$_1$-C$_{10}$ linear or branched alkyl, C$_1$-C$_{10}$ alkoxyalkyl, C$_1$-C$_{10}$ fluoroalkyl, C$_4$-C$_{12}$ cycloaliphatic, and C$_6$-C$_{12}$ aryl; R$^2$ is selected from the group consisting of hydrogen, C$_1$-C$_{10}$ linear or branched alkyl, C$_1$-C$_{10}$ fluoroalkyl, C$_1$-C$_{10}$ alkoxy, C$_4$-C$_{12}$ cycloaliphatic, and C$_4$-C$_{12}$ aryl; L$_1$ is selected from the group consisting of an organic amide having a formula RCONR'R" wherein R and R' are independently linear or branched alkyl having from 1-10 carbon atoms wherein R and R' can be connected to form a cyclic group having from 4 to 6 atoms, and R" is selected from C$_1$-C$_4$ alkyl and C$_3$-C$_8$ cycloalkyl; L$_2$ is selected from the group consisting of H$_2$O and ROH wherein R is a C$_1$-C$_{10}$ linear or branched alkyl group or a cyclic group having from 4 to 6 atoms, and an organic amide having a formula RCONR'R" wherein R and R' are independently linear or branched alkyl having from 1-10 carbon atoms wherein R and R' can be connected to form a cyclic group having from 4 to 6 atoms, and R" is selected from the group consisting of a C$_1$-C$_4$ alkyl and a C$_4$-C$_8$ cycloalkyl; n is a number selected from between 1 and 4; m is selected from a number between 0 to 4, and p is selected from 1 and 2; and, (ii) Group 2 beta-ketoiminate with organic amides as adducts with a formula of [M(R$^1$C(O)CR$^2$C(NR$^3$)R$^4$)$_2$(μ-L)$_n$L$_m$]$_p$ wherein M is selected from Mg, Ca, Sr, and Ba; R$^1$, R$^3$, and R$^4$ are independently selected from the group consisting of C$_1$-C$_{10}$ linear or branched alkyl, C$_1$-C$_{10}$ alkoxyalkyl, C$_1$-C$_{10}$ fluoroalkyl, C$_4$-C$_{12}$ cycloaliphatic, and C$_4$-C$_{12}$ aryl; R$^2$ is selected from the group consisting of hydrogen, C$_1$-C$_{10}$ linear or branched alkyl, C$_1$-C$_{10}$ fluoroalkyl, C$_1$-C$_{10}$ alkoxy, C$_4$-C$_{12}$ cycloaliphatic, and C$_4$-C$_{12}$ aryl; L is selected from the group consisting of an organic amide having the formula RCONR'R" wherein R and R' are independently linear or branched alkyl having from 1-10 carbon atoms wherein R and R' can be connected to form a cyclic group having from 4 to 6 atoms, and R" is selected from the group consisting of C$_1$-C$_4$ alkyl and C$_4$-C$_8$ cycloalkyl; n is a number selected from between 0 and 4; m is selected from a number between 1 to 4, or n is a number selected from between 1 and 4 and m is a number selected from between 0 to 4; p is selected from 1 and 2; and μ-L indicates that L is connected to two metals, M, via μL's oxygen atom when p=2.

(iii) Group 2 amidinates with organic amides as adducts with a formula of [M(R$^1$NC(R$^2$)NR$^3$)$_2$(μ-L)$_n$L$_m$]$_p$ wherein M is selected from Mg, Ca, Sr, and Ba; R$^1$ and R$^3$ are independently selected from the group consisting of C$_1$-C$_{10}$ linear or branched alkyl, C$_1$-C$_{10}$ alkoxyalkyl, C$_1$-C$_{10}$ fluoroalkyl, C$_4$-C$_{12}$ cycloaliphatic, and C$_4$-C$_{12}$ aryl; R$^2$ is selected from the group consisting of hydrogen, C$_1$-C$_{10}$ linear or branched alkyl, C$_1$-C$_{10}$ fluoroalkyl, C$_1$-C$_{10}$ alkoxy, C$_4$-C$_{12}$ cycloaliphatic, and C$_4$-C$_{12}$ aryl; L is either bridging between two metal atoms or coordinating to one metal atom through the oxygen atom and is selected from the group of an organic amide having the formula RCONR'R" wherein R and R' are independently linear or branched alkyl having from 1-10 carbon atoms wherein R and R' can be connected to form a cyclic group having from 4 to 6 atoms, and R" is selected from the group consisting of C$_1$-C$_4$ alkyl and C$_4$-C$_8$ cycloalkyl; n is a number selected from between 0 and 4; m is selected from a number between 1 to 4, or n is a number selected from between 1 and 4 and m is a number selected from between 0 to 4; p is selected from 1, 2; and μ-L indicates L is connected to two metals, M, via μL's oxygen atom when p=2.

This invention is related to Group 2 metal-containing complexes having both beta-ketonate or beta-ketoiminate or amidinate and organic amides and their solutions, which are useful for fabricating conformal metal containing films on substrates such as silicon, metal nitride, metal oxide and other metal layers via deposition processes, e.g., chemical vapor deposition (CVD), plasma enhanced chemical vapor deposition (PECVD), low pressure chemical vapor deposition (LPCVD), plasma enhanced atomic layer deposition (PE ALD) and atomic layer deposition (ALD). Such conformal metal containing films have applications ranging from computer chips, optical device, magnetic information storage, to metallic catalyst coated on a supporting material. In contrast to prior polydentate beta-ketoiminate precursors, the polydentate beta-ketoiminate ligands incorporate at least one amino organo imino functionality, which is in contrast to the literatures reported alkoxy group as the donating ligand.

One type of structure in the metal precursor is illustrated in structure A below where the metal M is a Group 2 metal having the formula:

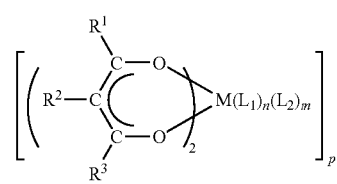

A wherein M is selected from Mg, Ca, Sr, and Ba; R$^1$ and R$^3$ are independently selected from the group consisting of C$_1$-C$_{10}$ linear or branched alkyl, C$_1$-C$_{10}$ alkoxyalkyl, C$_1$-C$_{10}$ fluoroalkyl, C$_4$-C$_{12}$ cycloaliphatic, and C$_4$-C$_{12}$ aryl (i.e. where R$^1$ and/or R$^3$ are alkyl, alkoxyalkyl, or fluoroalkyl they may have from 1 to 10 carbon atoms, and where R$^1$ and/or R$^3$ are cycloaliphatic or aryl they may have from 4 to 12 carbon atoms); R$^2$ is selected from the group consisting of hydrogen, C$_1$-C$_{10}$ linear or branched alkyl, C$_1$-C$_{10}$ fluoroalkyl, C$_1$-C$_{10}$ alkoxy, C$_4$-C$_{12}$ cycloaliphatic, and C$_6$-C$_{12}$ aryl (i.e. where R$^2$ is alkyl, alkoxyalkyl, or fluoroalkyl it may have from 1 to 10 carbon atoms, where R$^2$ is cycloaliphatic it may have from 4 to 12 carbon atoms, or where R$^2$ is aryl it may have from 6 to 12 carbon atoms); L$_1$ is selected from the group consisting of an organic amide having a formula RCONR'R" wherein R and R' are independently linear or branched alkyl having from 1-10 carbon atoms wherein R and R' can be connected to form a cyclic group having from 4 to 6 atoms, and R" is selected from the group consisting of C$_1$-C$_4$ alkyl and C$_3$-C$_8$ cycloalkyl; L$_2$ is selected from the group consisting of H$_2$O and ROH wherein R is a C$_1$-C$_{10}$ linear or branched alkyl group or a cyclic group having from 4 to 6 atoms, and an organic amide having a formula RCONR'R" wherein R and R' are linear or branched alkyl having from 1-10 carbon atoms wherein R and R' can be connected to form a cyclic group having from 4 to 6 atoms, and R" is selected from a C$_1$-C$_4$ alkyl and a C$_4$-C$_8$ cycloalkyl; n is a number selected from between 1 and 4; m is selected from a number between 0 to 4, and p is selected from 1 and 2.

Another type of structure in the metal precursor is illustrated in structure B below where the metal M is a Group 2 metal having the formula:

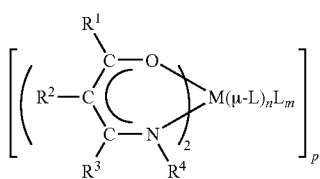

wherein M is selected from Mg, Ca, Sr, and Ba; $R^1$, $R^3$, and $R^4$ are independently selected from the group consisting of $C_1$-$C_{10}$ linear or branched alkyl, $C_1$-$C_{10}$ alkoxyalkyl, $C_1$-$C_{10}$ fluoroalkyl, $C_4$-$C_{12}$ cycloaliphatic, and $C_4$-$C_{12}$ aryl (i.e. where $R^1$ and/or $R^4$ are alkyl, alkoxyalkyl, or fluoroalkyl they may have from 1 to 10 carbon atoms, and where they are cycloaliphatic or aryl they may have from 4 to 12 carbon atoms); $R^2$ is selected from the group consisting of hydrogen, $C_1$-$C_{10}$ linear or branched alkyl, $C_1$-$C_{10}$ fluoroalkyl, $C_1$-$C_{10}$ alkoxy, $C_4$-$C_{12}$ cycloaliphatic, and $C_4$-$C_{12}$ aryl (i.e. where $R^2$ is alkyl, alkoxyalkyl, or fluoroalkyl they may have from 1 to 10 carbon atoms, and where they are cycloaliphatic or aryl they may have from 4 to 12 carbon atoms); L is selected from the group consisting of an organic amide having the formula RCONR'R" wherein R and R' are independently linear or branched alkyl having from 1-10 carbon atoms wherein R and R' can be connected to form a cyclic group having from 4 to 6 atoms, and R" is selected from the group consisting of $C_1$-$C_4$ alkyl and $C_4$-$C_8$ cycloalkyl; n is a number selected from between 0 and 4; m is selected from a number between 1 to 4, or n is a number selected from between 1 and 4 and m is a number selected from between 0 to 4; p is selected from 1 and 2; and β-L indicates that L is connected to two metals, M, via μL's oxygen atom when p=2.

The third type of structure in the metal precursor is illustrated in structure C below where the metal M is a Group 2 metal having the formula:

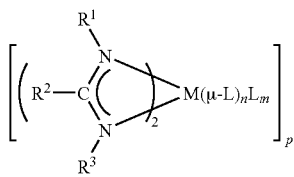

wherein M is selected from Mg, Ca, Sr, and Ba; $R^1$ and $R^3$ are independently selected from the group consisting of $C_1$-$C_{10}$ linear or branched alkyl, $C_1$-$C_{10}$ alkoxyalkyl, $C_1$-$C_{10}$ fluoroalkyl, $C_4$-$C_{12}$ cycloaliphatic, and $C_4$-$C_{12}$ aryl (i.e. where $R^1$ and/or $R^3$ are alkyl, alkoxyalkyl, or fluoroalkyl they may have from 1 to 10 carbon atoms, and where they are cycloaliphatic or aryl they may have from 4 to 12 carbon atoms); $R^2$ is selected from the group consisting of hydrogen, $C_1$-$C_{10}$ linear or branched alkyl, $C_1$-$C_{10}$ fluoroalkyl, $C_1$-$C_{10}$ alkoxy, $C_4$-$C_{12}$ cycloaliphatic, and $C_4$-$C_{12}$ aryl (i.e. where $R^2$ is alkyl, alkoxyalkyl, or fluoroalkyl it may have from 1 to 10 carbon atoms, and where it is cycloaliphatic or aryl it may have from 4 to 12 carbon atoms); L is selected from the group of an organic amide having the formula RCONR'R" wherein R and R' are independently linear or branched alkyl having from 1-10 carbon atoms wherein R and R' can be connected to form a cyclic group having from 4 to 6 atoms, and R" is selected from the group consisting of $C_1$-$C_4$ alkyl and $C_4$-$C_8$ cycloalkyl; n is a number selected from between 0 and 4; m is selected from a number between 1 to 4, or n is a number selected from between 1 and 4 and m is a number selected from between 0 to 4; p is selected from 1 and 2; and μ-L indicates L is connected to two metals, M, via μL's oxygen atom when p=2.

In preferred embodiments of the present invention, n+m=4 or less. Preferably, where p=2, n is a number selected from between 1 and 2, and m is a number selected from between 0 and 2.

L, $L_1$ and $L_2$ are preferably selected from organic amides such as N-methyl pyrrolidinone (NMP), N,N-Diethylformamide (DEF), N,N-Diethylacetamide (DEAC), N,N-Dimethylacetamide (DMAC), N-cyclohexyl 2-pyrrolidinone and, in the case of $L_2$, $H_2O$ and ROH. In addition to NMP and N-cyclohexyl 2-pyrrolidinone, other N-substituted lactams (i.e. other organic amides of the class RCONR'R" wherein R and R' are alkyl and are connected to form with the C and N a 4-6 membered cyclic group, and R" is selected from alkyl having from 1 to 4 carbon atoms and cycloalkyl having from 4 to 8 carbon atoms) also constitute preferred organic amides.

Where the metal containing complex is of structure A and p=2, $L_1$ is preferably connected to both metals, M, via $L_1$'s oxygen atom.

Where the metal containing complex is of structure A, $R^1$ and $R^3$ are preferably selected from t-butyl and t-pentyl, and $R^2$ is preferably selected from hydrogen, methyl and ethyl.

In one embodiment, the metal containing complex is of structure A, M is strontium, $R^1$ and $R^3$ are each t-butyl, $R^2$ is hydrogen, $L_1$ and $L_2$ are each N-methyl-pyrrolidone, n=1.5, m=0.5, and p=2.

In another embodiment, the metal containing complex is of structure A, M is strontium, $R^1$ and $R^3$ are each t-butyl, $R^2$ is hydrogen, $L_1$ is N,N-Diethylacetamide (DEAC), n=1.5, m=0, and p=2.

In yet another embodiment, the metal containing complex is of structure A, M is barium, $R^1$ and $R^3$ are each $CF_3$, $R^2$ is hydrogen, $L_1$ and $L_2$ are each N-methyl-pyrrolidone, n=1.5, m=2, and p=2.

In yet another embodiment, the metal containing complex is of structure A, M is barium, $R^1$ and $R^3$ are each t-butyl, $R^2$ is hydrogen, $L_1$ is N N-methyl-pyrrolidone, n=2, $L_2$=$H_2O$, m=1, and p=2.

Where the metal containing complex is of structure B, $R^1$ and $R^3$ are preferably independently selected from t-butyl and t-pentyl; $R^2$ is preferably selected from hydrogen, methyl and ethyl; and $R^4$ is preferably selected from iso-propyl, t-butyl, sec-butyl, t-pentyl and mixtures thereof.

Where the metal containing complex is of structure C, $R^1$ and $R^3$ are preferably independently selected from the t-butyl and t-pentyl; and $R^2$ is preferably selected from hydrogen, methyl and ethyl.

Exemplary preferred metal containing complexes include: $Ba_2(1,1,1,5,5,5$-hexafluoro-2,4-pentanedione$)_4$(N-methylpyrrolidinone$)_5$; $Sr_2(2,2,6,6$-tetramethyl-3,5-heptanedione$)_4$(N-methylpyrrolidinone$)_4$; $Sr_2(2,2,6,6$-tetramethyl-3,5-heptanedione$)_4$(N,N-Diethylacetamide$)_3$; $Ba_2(2,2,6,6$-tetramethyl-3,5-heptanedione$)_4$(N-methylpyrrolidinone$)_4$.($H_2O)_2$; bis(2,2-dimethyl-5-(iso-propylamino)-3-hexanonato)barium(N-methylpyrrolidinone); bis(2,2-dimethyl-5-(sec-butylamino)-3-hexanonato)strontium(N-methylpyrrolidinone); and bis(2,2-dimethyl-5-(sec-butylamino)-3-hexanonato)strontium(N,N-Diethylacetamide).

In a preferred embodiment, the metal containing complex is dissolved in a solvent selected from glyme solvents having from 1 to 20 ethoxy —($C_2H_4O$)— repeat units; $C_2$-$C_{12}$ alkanols; organic ethers; $C_6$-$C_{12}$ aliphatic hydrocarbons; $C_6$-$C_{18}$ aromatic hydrocarbons; organic esters; organic amines; and polyamines and organic amides. Organic ethers selected from dialkyl ethers comprising $C_1$-$C_6$ alkyl moieties, $C_4$-$C_8$ cyclic ethers, and $C_{12}$-$C_{60}$ crown $O_4$-$O_{20}$ ethers (wherein C is the number of carbon atoms in the crown ether compound and O is the number of oxygen atoms in the crown ether), and organic amides selected from N-methylpyrrolidinone ("NMP"), N,N-Diethylformamide (DEF), N,N-Diethylacetamide (DEAC), N,N-Dimethylacetamide (DMAC), and N-cyclohexyl 2-pyrrolidinone, are in particular preferred.

These metal-containing complexes having both beta-ketonate or beta-ketoiminate ligands and organic amides can be employed as precursors to make thin metal or metal oxide films via either the chemical vapor deposition (CVD) or atomic layer deposition (ALD) method at temperatures less than 500° C. The CVD process can be carried out with or without reducing or oxidizing agents, whereas an ALD process usually involves the employment of another reactant, such as a reducing agent or oxidizing agent.

For multi-component metal oxides such as STO and BST, these metal-containing complexes, having beta-ketonate or beta-ketoiminate or amidinate ligands and organic amides, can be delivered in vapor phase into a CVD or ALD reactor via well-known bubbling or vapor draw techniques as strontium or barium sources. The titanium source is selected from titanium alkoxides or beta-diketonates such as Ti($OPr^i$)$_4$, Ti(tmhd)$_2$($OPr^i$)$_2$, where $Pr^i$=isopropyl, where tmhd=2,2,6,6-tetramethyl-3,5-heptanedionate, Ti(mpd)(tmhd)$_2$, where mpd=2-methyl-2,4-pentanedioxy, Ti(4-(2-methylethoxy)imino-2-pentanoate)$_2$, and analogous titanium ligands and derivatives. A direct liquid delivery method can also be employed by dissolving the titanium, strontium as well as barium complexes in a suitable solvent or a solvent mixture to prepare a solution with a molar concentration from 0.001 to 2 M, depending the solvent or mixed-solvents employed. Oxidizing agents for the deposition process include oxygen, water, hydrogen peroxide, oxygen plasma, nitrous oxide, and ozone. In a preferred embodiment, the multi-component metal oxide films are grown in the temperature range of 200 to 500° C., preferably 250 to 350° C. whereby an amorphous STO or BST films are obtained. A thermal annealing is needed to convert the resulting films from amorphous into crystalline form. The annealing can be conducted at a higher temperature 500 to 1200° C. under oxidizing conditions, preferably in the range of 500 to 700° C. for high k dielectrics in DRAM applications. The thickness of the STO or BST film is in the range of 1 nm to 500 nm, preferably 2 nm to 10 nm, deposited on compatible substrates including platinum(Pt), $RuO_2$, $SrRuO_3$, silica, silicon nitride, and silicon. The process chamber pressure may preferably be from about 0.1 Torr to 100 Torr, and more preferably from about 0.1 Torr to 5 Torr.

The solvent employed in solubilizing the precursor for use in a deposition process may comprise any compatible solvent or their mixture, including: aliphatic hydrocarbons, aromatic hydrocarbons, ethers, esters, nitrites, and alcohols. The solvent component of the solution preferably comprises a solvent selected from the group consisting of: glyme solvents having from 1 to 20 ethoxy —($C_2H_4O$)— repeat units; $C_2$-$C_{12}$ alkanols, organic ethers selected from the group consisting of dialkyl ethers comprising $C_1$-$C_6$ alkyl moieties, $C_4$-$C_8$ cyclic ethers; $C_{12}$-$C_{60}$ crown $O_4$-$O_{20}$ ethers (wherein C is the number of carbon atoms in the ether compound and O is the number of oxygen atoms in the ether compound); $C_6$-$C_{12}$ aliphatic hydrocarbons; $C_6$-$C_{18}$ aromatic hydrocarbons; organic esters; organic amines, polyamines and organic amides.

Another class of solvents that offers advantages is the organic amide class of the form RCONR'R", wherein R and R' are independently linear or branched alkyl having from 1-10 carbon atoms, and they can be connected to form a cyclic group ($CH_2$)$_q$, wherein q is from 4-6, preferably 5, and R" is selected from alkyl having from 1 to 4 carbon atoms and cycloalkyl having 4 to 8 carbon atoms. N-methylpyrrolidinone (NMP), N,N-Diethylformamide (DEF), N,N-Diethylacetamide (DEAC), N,N-Dimethylacetamide (DMAC), and N-cyclohexyl 2-pyrrolidinone are examples.

The following examples illustrate the preparation of the metal-containing complexes with beta-diketone or beta-ketoiminate ligands as well as their use as precursors in metal-containing film deposition processes.

Example 1

Synthesis of $Ba_2(hfac)_4(NMP)_5$ 0.52 g (3.80 mmol) of $BaH_2$ was loaded in flask with 15 mL of toluene. To this flask was added 2.15 g (21.70 mmol) NMP followed by addition of 1.57 g (7.60 mmol) 1,1,1,5,5,5-hexafluoro-2,4-pentanedione ("hfac"). The reaction mixture was stirred at room temperature until bubbling ceased after 5-10 minutes. Removal of all volatiles under vacuum afforded an oily white solid. Recrystallization from hexanes at −40° C. provided colorless which were identified by crystal structure analysis as the dimer $Ba_2(hfac)_4(NMP)_5$.

Example 2

Synthesis of $Sr_2(tmhd)_4(NMP)_4$ 0.50 g (5.58 mmol) of $SrH_2$ was loaded into a 100 mL Schlenk flask with 5 g of NMP. To this flask was added 2.06 g (11.16 mmol) 2,2,6,6-tetramethyl-3,5-heptanedione ("tmhd") in 5 g of NMP and bubbling occurred. The reaction mixture was stirred over night at room temperature. The reaction mixture was subjected to vacuum transferred at 65-70° C. leaving behind a grey solid weighing 2.86 g. Recrystallization in a 1:1 solution of hexane to pentane in −40° C. freezer afforded clear needle like crystals that were identified by crystal structure analysis as the dimer $Sr_2(tmhd)_4(NMP)_4$.

Example 3

Synthesis of $Sr_2(tmhd)_4(DEAC)_3$

To a suspension of 0.50 g (5.58 mmol) $SrH_2$ in hexanes was added 20.10 g (11.16 mmol) 2,2,6,6-tetramethyl-3,5-heptanedione ("tmhd") and 2.60 g (22.32 mmol) N,N-diethylacetamide (DEAC) in hexanes at room temperature. Bubbling and heat were given off and the suspension turned to clear solution after approximately 10 minutes. The reaction mixture was stirred for 16 hours and removal of hexanes afforded an oil that was set up for vacuum transfer and heated at 80° C. under 300 mTorr for several hours. 2.38 g of clear residual slurry (68% yield) was collected and recrystallization in pentane at −40° C. gave rise to clear crystals. The crystals were identified by crystal structure analysis as $Sr_2(tmhd)_4(DEAC)_3$.

Example 4

Synthesis of Ba$_2$(tmhd)$_4$(NMP)$_4$(H$_2$O)$_2$ 0.50 g (3.59 mmol) of BaH2 was loaded into a 100 mL Schlenk flask with 15 mL of hexane. To this flask was added a solution of 1.32 g (7.18 mmol) tmhd and 1.42 (14.35 mmol) NMP in 5 mL hexane and bubbling was witnessed. After approximately 6 hours, the hexane was evaporated under vacuum leaving behind a grey solid weighing 2.32 g. Recrystallization in octane gave rise to clear hexagonal-like crystals that were analyzed by crystal structure analysis to a dimer. The yield was 90%.

Example 5

Synthesis of 2,2-dimethyl-5-(iso-propylamino)-3-hexanone

To a solution of 15.00 g (105.49 mmol) 2,2-dimethyl-3,5-hexanedione in 50 mL of toluene loaded with 30.00 g sodium sulfate was added 12.47 g (210.97 mmol) isopropylamine. The mixture was refluxed for 4 days. Removal of toluene resulted in a yellow oil, which was subjected to vacuum transfer at 80° C. under 125 mTorr. 16.5 g of clear oil was obtained with a yield of 84%. $^1$H NMR (500 MHz, C$_6$D$_6$): δ=11.50 (s, 1H), 5.16 (s, 1H), 3.11 (m, 1H), 1.49 (s, 3H), 1.31 (s, 9H), 0.79 (d, 6H).

Example 6

Synthesis of 2,2-dimethyl-5-(sec-butylamino)-3-hexanone

To a solution of 5.00 g (35.16 mmol) 2,2-dimethyl-3,5-hexanedione in 20 mL of toluene loaded with 10.00 g of sodium sulfate was added 5.14 g (70.32 mmol) sec-butylamine. The mixture was refluxed 3 days. 4.90 g of light yellow oil was obtained after work-up. The isolated yield was 71%. $^1$H NMR (500 MHz, C$_6$D$_6$): δ=11.52 (s, 1H), 5.18 (s, 1H), 2.95 (m, 1H), 1.51 (s, 3H), 1.31 (s, 9H), 1.14 (s, 2H), 0.80 (d, 3H), 0.67 (t, 3H).

Example 7

Synthesis of bis(2,2-dimethyl-5-(iso-propylamino)-3-hexanonato)barium NMP Adduct To a suspension of 1 g (1.66 mmol) Ba(N(SiMe$_3$)$_2$)$_2$(THF)$_2$ in hexane was added 0.61 g (3.32 mmol) of 2,2-dimethyl-5-(iso-propylamino)-3-hexanone and 0.66 g (6.64 mmol) of NMP in hexane at room temperature. The reaction mixture turned to solution after approximately 30 minutes. After stirring for 16 hours, hexane was evaporated under vacuum to provide 0.95 g of a white solid. The white solid was heated in hexane, filtered, and recrystallized an −40° C. to give rise to foggy-white crystals. $^1$H NMR (500 MHz, C$_6$D$_6$): δ=5.06 (s, 1H), 3.75 (m, 1H), 2.42 (s, 3H), 2.40 (t, 2H), 1.98 (t, 2H), 1.83 (s, 3H), 1.44 (s, 9H), 1.34 (d, 6H), 1.17 (m, 2H).

Example 8

Synthesis of bis(2,2-dimethyl-5-(sec-butylamino)-3-hexanonato)strontium NMP Adduct To a solution of 1 g (1.81 mmol) of Sr(N(SiMe$_3$)$_2$)$_2$(THF)$_2$ in hexanes was added 0.66 g (3.62 mmol) of 2,2-dimethyl-5-(sec-butylamino)-3-hexanone and 0.72 g (7.24 mmol) of NMP in hexanes at room temperature. After stirring for 16 hours, hexanes were evaporated under vacuum. Recrystallization in hexanes at −20° C. resulted in a opaque white solid. $^1$H NMR (500 MHz, C$_6$D$_6$): δ=5.06 (s, 1H), 3.75 (m, 1H), 2.46 (s, 3H), 2.42 (t, 2H), 2.07 (t, 2H), 1.90 (s, 3H), 1.47 (s, 9H), 1.47 (d, 6H), 1.21 (m, 2H).

Example 9

Synthesis of bis(2,2-dimethyl-5-(sec-butylamino)-3-hexanonato)strontium DEAC Adduct To a solution of 1 g (1.81 mmol) Sr(N(SiMe$_3$)$_2$)$_2$(THF)$_2$ in 10 mL hexanes at room temperature was added 0.71 g (3.62 mmol) of 2,2-dimethyl-5-(sec-butylamino)-3-hexanone and 0.83 g (7.24 mmol) DEAC in 10 mL hexanes. Reaction was stirring for 16 hours. Evaporation of hexanes afforded a wet off-white solid. $^1$H NMR (500 MHz, C$_6$D$_6$): δ=5.05 (s, 1H), 3.59 (m, 1H), 3.17 (q, 2H), 2.51 (q, 2H), 1.96 (s, 3H), 1.79 (s, 3H), 1.55 (s, 9H) 1.44 (m, 2H), 1.44 (d, 3H), 1.03 (t, 3H) 0.96 (t, 3H), 0.56 (t, 3H).

The foregoing examples and description of the preferred embodiments should be taken as illustrating, rather than as limiting the present invention as defined by the claims. As will be readily appreciated, numerous variations and combinations of the features set forth above can be utilized without departing from the present invention as set forth in the claims. Such variations are not regarded as a departure from the spirit and scope of the invention, and all such variations are intended to be included within the scope of the following claims.

The invention claimed is:

1. A metal containing complex represented by the structure:

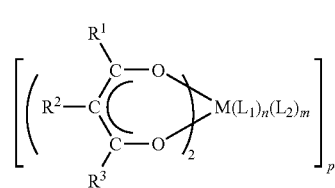

wherein M is selected from Ca, Sr, Ba, and mixtures thereof; R$^1$ and R$^3$ are independently selected from the group consisting of C$_1$-C$_{10}$ linear or branched alkyl, C$_1$-C$_{10}$ alkoxyalkyl, C$_1$-C$_{10}$ fluoroalkyl, C$_4$-C$_{12}$ cycloaliphatic, and C$_4$-C$_{12}$ aryl; R$^2$ is selected from the group consisting of hydrogen, C$_1$-C$_{10}$ linear or branched alkyl, C$_1$-C$_{10}$ fluoroalkyl, C$_1$-C$_{10}$ alkoxy, C$_4$-C$_{12}$ cycloaliphatic, and C$_6$-C$_{12}$ aryl; L$_1$ is an organic amide having a formula RCONR'R" wherein R and R' are independently linear or branched alkyl having from 1-10 carbon atoms wherein R and R' can be connected to form a cyclic group having from 4 to 6 atoms, and R" is selected from the group consisting of C$_1$-C$_4$ alkyl and C$_4$-C$_8$ cycloalkyl; L$_2$ is selected from the group consisting of H$_2$O and ROH wherein R is a C$_1$-C$_{10}$ linear or branched alkyl group or a cyclic group having from 4 to 6 atoms, and an organic amide having a formula RCONR'R" wherein R and R' are linear or branched alkyl having from 1-10 carbon atoms wherein R and R' can be connected to form a cyclic group having from 4 to 6 atoms, and R" is selected from the group consisting of a C$_1$-C$_4$ alkyl and a C$_3$-C$_8$ cycloalkyl; n is a number selected from between 1 and 4; m is selected from a number between 0 to 4, and p is selected from 1 and 2.

2. The metal containing complex of claim 1 wherein $L_1$ and $L_2$ are selected from the group consisting of N-methylpyrrolidinone (NMP), N,N-Diethylacetamide (DEAC), N,N-Dimethylacetamide (DMAC), N-cyclohexyl 2-pyrrolidinone, $H_2O$, and ROH.

3. The metal containing complex of claim 1 wherein $R^1$ and $R^3$ are selected from the group consisting of t-butyl and t-pentyl; and $R^2$ is selected from the group consisting of hydrogen, methyl and ethyl.

4. The metal containing complex of claim 1 wherein M is strontium; $R^1$ and $R^3$ are each t-butyl, $R^2$ is hydrogen, $L_1$ and $L_2$ are each N-methyl-pyrrolidone, n=1.5, m=0.5, and p=2.

5. The metal containing complex of claim 1 wherein M is strontium; $R^1$ and $R^3$ are each t-butyl; $R^2$ is hydrogen; $L_1$ is N,N-Diethylacetamide (DEAC); n=1.5; m=0; and p=2.

6. The metal containing complex of claim 1 wherein M is barium; $R^1$ and $R^3$ are each $CF_3$; $R^2$ is hydrogen; $L_1$ and $L_2$ are each N-methyl-pyrrolidone; n=1.5; m=2; and p=1.

7. The metal containing complex of claim 1 wherein M is barium; $R^1$ and $R^3$ are each t-butyl; $R^2$ is hydrogen; $L_1$ is N N-methyl-pyrrolidone; n=2; $L_2=H_2O$; m=1; and p=2.

8. The metal containing complex of claim 1 dissolved in a solvent selected from the group consisting of glyme solvents having from 1 to 20 ethoxy —$(C_2H_4O)$— repeat units; $C_2$-$C_{12}$ alkanols, organic ethers; $C_6$-$C_{12}$ aliphatic hydrocarbons; $C_6$-$C_{18}$ aromatic hydrocarbons; organic esters; organic amines; and polyamines and organic amides.

9. The metal containing complex of claim 8 wherein the solvent is an organic ether selected from the group consisting of dialkyl ethers comprising $C_1$-$C_6$ alkyl moieties, $C_4$-$C_8$ cyclic ethers; $C_{12}$-$C_{60}$ crown $O_4$—$O_{20}$ ethers (wherein C is the number of carbon atoms in the crown ether compound and O is the number of oxygen atoms in the crown ether.

10. The metal containing complex of claim 8 wherein the solvent is an organic amide selected from the group consisting of N-methylpyrrolidinone ("NMP"), N,N-Diethylacetamide (DEAC), N,N-Dimethylacetamide (DMAC), and N-cyclohexyl 2-pyrrolidinone.

11. A vapor deposition process for forming a conformal multi-component metal oxide thin film on a substrate wherein at least two metal containing complexes and an oxygen containing agent are introduced to a deposition chamber and a multi-component metal oxide film is deposited on a substrate, the improvement which comprises using at least two metal containing complexes, having different metals, selected from:

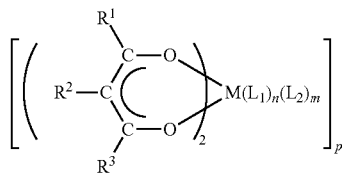

A wherein M is selected from Ca, Sr, and Ba; $R^1$ and $R^3$ are independently selected from the group consisting of $C_1$-$C_{10}$ linear or branched alkyl, $C_1$-$C_{10}$ alkoxyalkyl, $C_1$-$C_{10}$ fluoroalkyl, $C_4$-$C_{12}$ cycloaliphatic, and $C_4$-$C_{12}$ aryl; $R^2$ is selected from the group consisting of hydrogen, $C_1$-$C_{10}$ linear or branched alkyl, $C_1$-$C_{10}$ fluoroalkyl, $C_1$-$C_{10}$ alkoxy, $C_4$-$C_{12}$ cycloaliphatic, and $C_6$-$C_{12}$ aryl; $L_1$ is an organic amide having a formula RCONR'R" wherein R and R' are independently linear or branched alkyl having from 1-10 carbon atoms wherein R and R' can be connected to form a cyclic group having from 4 to 6 atoms, and R" is selected from the group consisting of $C_1$-$C_4$ alkyl and $C_4$-$C_8$ cycloalkyl; $L_2$ is selected from the group consisting of $H_2O$ and ROH wherein R is a $C_1$-$C_{10}$ linear or branched alkyl group or a cyclic group having from 4 to 6 atoms, and an organic amide having a formula RCONR'R" wherein R and R' are independently linear or branched alkyl having from 1-10 carbon atoms wherein R and R' can be connected to form a cyclic group having from 4 to 6 atoms, and R" is selected from the group consisting of a $C_1$-$C_4$ alkyl and a $C_4$-$C_8$ cycloalkyl; n is a number selected from between 1 and 4; m is selected from a number between 0 to 4, and p is selected from 1 and 2.

12. The process of claim 11 wherein the vapor deposition process is selected from the group consisting of chemical vapor deposition, cyclic chemical vapor deposition and atomic layer deposition.

13. The process of claim 11 wherein the oxygen containing agent is selected from the group consisting of $N_2O$, $O_2$, $H_2O_2$, $H_2O$, ozone, $O_2$ plasma, $H_2O$ plasma, organic peroxide, and mixtures thereof.

14. The process of claim 11 wherein a first metal containing complex is selected from the group consisting of $Sr_2(tmhd)_4(NMP)_4$, and $Sr_2(tmhd)_4(DEAC)_3$, and a second metal containing complex is selected from the group consisting of $Ba_2(tmhd)_4(NMP)_4.(H_2O)_2$, $Ba_2(hfac)_4(NMP)_5$.

15. The process of claim 14 wherein a third metal containing complex is selected from the group consisting of titanium containing alkoxides and beta-ketonates and mixtures thereof.

16. The process of claim 15 wherein the third metal containing complex is selected from the group consisting of $Ti(OPr^i)_4$, $Ti(tmhd)_2(OPr^i)_2$, where $Pr^i$=isopropyl, where tmhd=2,2,6,6-tetramethyl-3,5-heptanedionate, Ti(mpd)(tmhd)$_2$, where mpd=2-methyl-2,4-pentanedioxy, Ti(4-(2-methylethoxy)imino-2-pentanoate)$_2$ and mixtures thereof.

* * * * *

UNITED STATES PATENT AND TRADEMARK OFFICE
CERTIFICATE OF CORRECTION

PATENT NO. : 8,247,617 B2  
APPLICATION NO. : 12/266058  
DATED : August 21, 2012  
INVENTOR(S) : Xinjian Lei, Liam J. Quinn and Daniel P. Spence Page 1 of 1

It is certified that error appears in the above-identified patent and that said Letters Patent is hereby corrected as shown below:

In the Claims:

Column 13, Line 18

In Claim 7 delete "N"

Signed and Sealed this  
Seventh Day of May, 2013

Teresa Stanek Rea  
*Acting Director of the United States Patent and Trademark Office*